(12) United States Patent
Kwon et al.

(10) Patent No.: US 11,419,644 B2
(45) Date of Patent: Aug. 23, 2022

(54) INTRAMEDULLARY ROD FOR BONE FIXATION

(71) Applicant: IKEY CO., LTD, Busan (KR)

(72) Inventors: Younguk Kwon, Busan (KR);
Changhyeong Kang, Busan (KR)

(73) Assignee: IKEY CO., LTD, Busan (KR)

( * ) Notice: Subject to any disclaimer, the term of this patent is extended or adjusted under 35 U.S.C. 154(b) by 456 days.

(21) Appl. No.: 16/527,651

(22) Filed: Jul. 31, 2019

(65) Prior Publication Data

US 2020/0113608 A1   Apr. 16, 2020

(30) Foreign Application Priority Data

Oct. 16, 2018   (KR) .................. 10-2018-0123219

(51) Int. Cl.
*A61B 17/72* (2006.01)
*A61B 17/84* (2006.01)
*A61B 17/74* (2006.01)
*A61B 17/17* (2006.01)

(52) U.S. Cl.
CPC ...... *A61B 17/7216* (2013.01); *A61B 17/7233* (2013.01); *A61B 17/7283* (2013.01); *A61B 17/1725* (2013.01); *A61B 17/744* (2013.01); *A61B 17/746* (2013.01); *A61B 17/84* (2013.01)

(58) Field of Classification Search
CPC ............ A61B 17/7216; A61B 17/7233; A61B 17/7283; A61B 17/1725; A61B 17/744; A61B 17/746; A61B 17/84; A61B 17/86; A61B 17/7225; A61B 17/725; A61B 17/7266; A61B 17/8061; A61B 17/72–7291

USPC ...................................... 606/62–64
See application file for complete search history.

(56) References Cited

U.S. PATENT DOCUMENTS

| 5,549,610 | A | * | 8/1996 | Russell ................. A61B 17/72 606/62 |
| 10,092,334 | B2 | * | 10/2018 | Sato ..................... A61B 17/744 |
| 10,695,109 | B2 | * | 6/2020 | Karg .................. A61B 17/7283 |
| 2011/0196372 | A1 | * | 8/2011 | Murase ................ A61B 17/744 606/64 |

FOREIGN PATENT DOCUMENTS

KR   10-1743051 B1   6/2017

* cited by examiner

*Primary Examiner* — Eduardo C Robert
*Assistant Examiner* — Steven J Cotroneo
(74) *Attorney, Agent, or Firm* — Novick, Kim & Lee, PLLC; Sang Ho Lee; Hyun Woo Shin

(57) ABSTRACT

Provided is an intramedullary (IM) rod for bone fixation. The IM rod is configured to be placed in an intramedullary cavity of a center portion of a part of a fractured bone which is required to be fixed to another part of the fractured bone, and lengthily extends in a direction of the part of the fractured bone, wherein the IM rod includes a plurality of guide holes configured to guide fasteners which are inserted through the part of the fractured bone and fastened to the other part of the fractured bone, and the plurality of guide holes include a main hole and a pair of sub-holes provided at positions forming vertices of a triangle together with the main hole.

2 Claims, 7 Drawing Sheets

INTRAMEDULLARY ROD FOR BONE FIXATION

CROSS-REFERENCE TO RELATED APPLICATION

This application claims the benefit of Korean Patent Application No. 10-2018-0123219 filed on Oct. 16, 2018, in the Korean Intellectual Property Office, the disclosure of which is incorporated herein in its entirety by reference.

BACKGROUND

1. Field

One or more embodiments relate to an intramedullary (IM) rod for bone fixation, and more particularly, to an IM rod having an improved structure to maintain a fixed state of a fractured bone for a long time after a medical procedure for fixing the fractured bone and prevent damage to the fractured bone during the medical procedure.

2. Description of the Related Art

In general, an intramedullary rod 110 (also known as an intramedullary nail, and will now be referred to as an "IM rod") is used to treat a fractured bone by placing the IM rod 110 in the center portion of the fractured bone, that is, the intramedullary cavity of the bone, for smooth fixation of the fractured bone as shown in FIG. 1.

Unlike the IM rod 110 configured to be inserted into the intramedullary cavity, a plate-type treatment unit 120 configured to be coupled to the outer surface of the fractured bone may also be used according to the bone fracture type of a patient.

Such bone treatment units of different types have different features and are thus used individually or in combination according to necessity.

Since the IM rod 110 is placed in the center of the fractured bone, that is, the intramedullary cavity of the fractured bone, the IM rod 110 smoothly withstands loads applied to the fractured bone in all directions on behalf of the fractured bone. However, since the IM rod 110 is placed in the intramedullary cavity through a joint portion or tissue around a joint, it is relatively difficult to perform a medical procedure using the IM rod 110, and a joint or adjacent tissue may be damaged.

In addition, as shown in FIG. 2, when a medical procedure is performed using an IM rod 210 to treat a femoral neck fracture, together with the IM rod 210, fasteners 220 are used which are inserted through the IM rod 210 and joined to a fractured bone portion. To prevent a decrease in fastening force caused by arbitrary rotations of the IM rod 210 and the fasteners 220 after fixation, two fasteners 220 are used.

However, since the fasteners 220 are joined to the fractured bone merely at relatively upper and lower positions along a straight line, rotation may not be completely prevented in a three-dimensional space, and thus the coupling states of the IM rod 210 and the fasteners 220 may not be securely maintained.

A related art document includes Korean Patent Registration No. 10-1743051.

SUMMARY

One or more embodiments include an intramedullary (IM) rod for bone fixation which is configured to securely maintain a fixed state of a fractured bone for a long time after a medical procedure for fixing a bone fracture such as a femoral neck fracture.

One or more embodiments include an IM rod for bone fixation which is configured to prevent damage to a bone during a medical procedure for fixing a bone fracture such as a femoral neck fracture.

Additional aspects will be set forth in part in the description which follows and, in part, will be apparent from the description, or may be learned by practice of the presented embodiments.

According to one or more embodiments, there is provided an IM rod for bone fixation, the IM rod being configured to be placed in an intramedullary cavity of a center portion of a part of a fractured bone which is required to be fixed to another part of the fractured bone, the IM rod lengthily extending in a direction of the part of the fractured bone, wherein the IM rod includes a plurality of guide holes configured to guide fasteners which are inserted through the part of the fractured bone and fastened to the other part of the fractured bone, and the plurality of guide holes include a main hole and a pair of sub-holes provided at positions forming vertices of a triangle together with the main hole.

The IM rod may further include: an intermediate diameter portion in which the main hole of the plurality of guide holes is formed; a large diameter portion in which the pair of sub-holes of the plurality of guide holes are formed and which has a diameter greater than a diameter of the intermediate diameter portion; and a small diameter portion which lengthily extends in an axial direction from the intermediate diameter portion and has a diameter less than the diameter of the intermediate diameter portion.

The small diameter portion may include deformable ribs between which a plurality of deformable slits are formed to allow bending deformation between adjacent elements such that damage caused by friction with an inner wall of the center portion of the part of the fractured bone may be suppressed.

The IM rod may further include a plurality of buffer members provided on mutually-facing inner surfaces of the deformable ribs at mutually contactable and separable positions, the plurality of buffer members including a buffering material such that the plurality of buffer members may perform a buffering function when being brought into contact with each other and may return to original shapes thereof when being separated from each other.

According to one or more embodiments, there is provided an IM rod for bone fixation, the IM rod being configured to be placed in an intramedullary cavity of a center portion of a part of a fractured bone which is required to be fixed to another part of the fractured bone, the IM rod lengthily extending in a direction of the part of the fractured bone, wherein the IM rod includes a plurality of guide holes configured to guide fasteners which are inserted through the part of the fractured bone and fastened to the other part of the fractured bone, wherein the plurality of guide holes include: a main hole; a pair of entrance-side sub-holes provided at positions forming vertices of a triangle together with the main hole; and two pairs of exit-side sub-holes forming different lines together with the pair of entrance-side sub-holes to adjust a fastening angle of the fasteners inserted through the entrance-side sub-holes.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
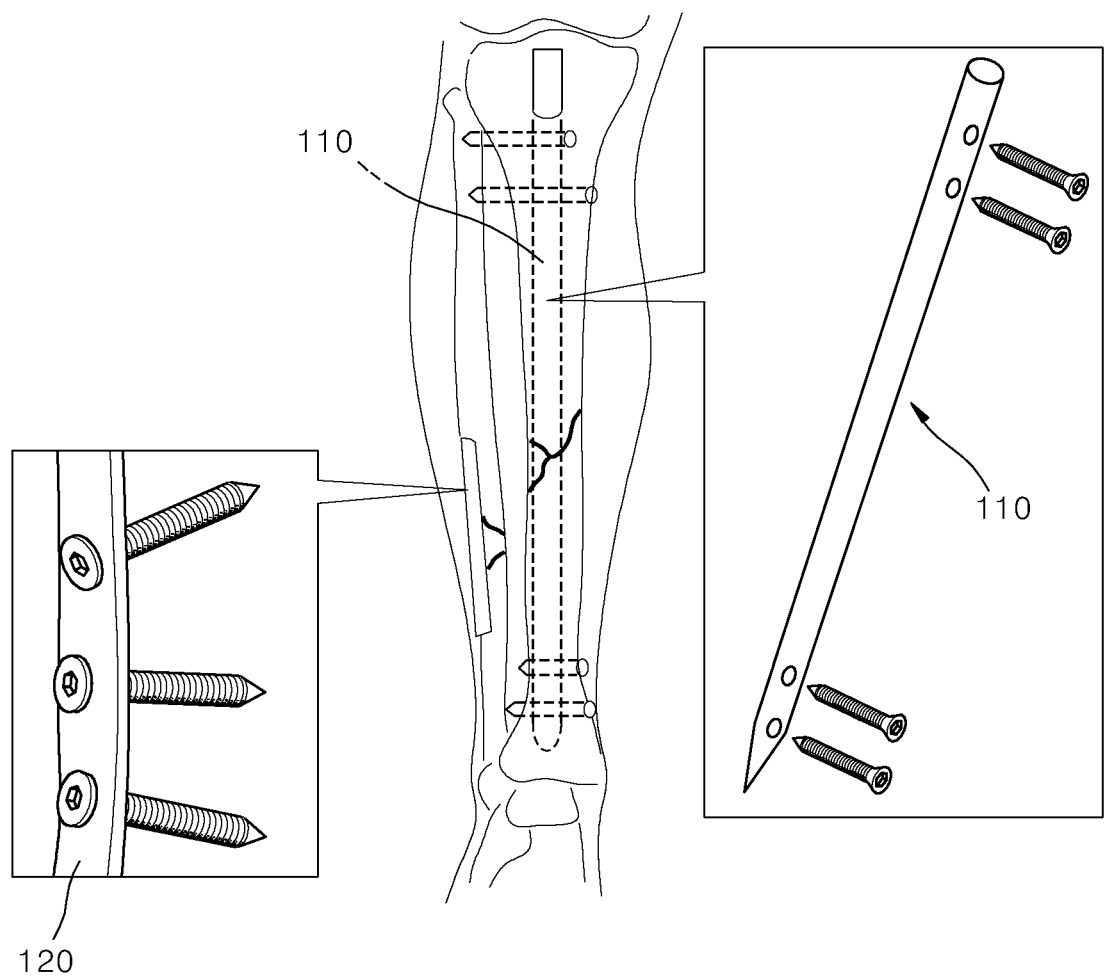
FIG. 1 is a view illustrating a schematic structure of a general bone fixing unit.
Figure 2:
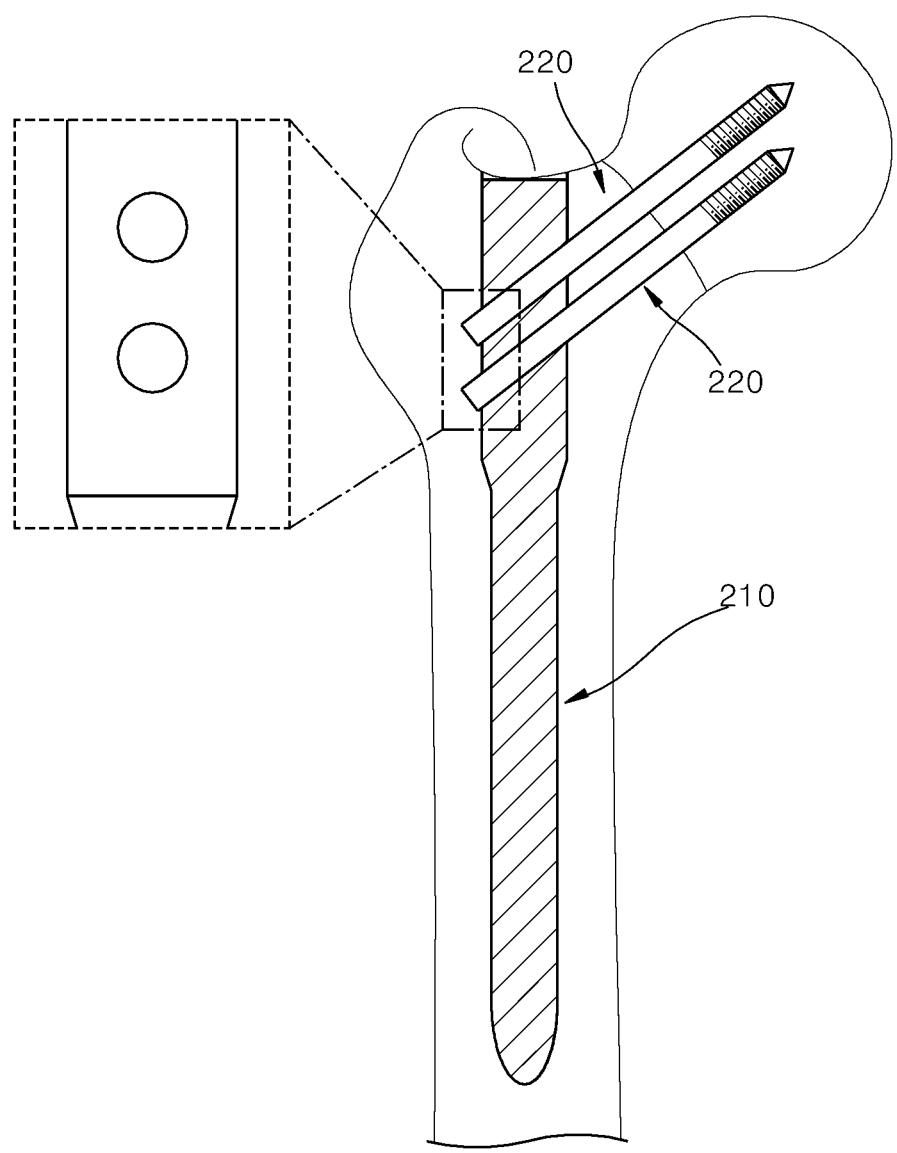
FIG. 2 is a view illustrating problems with an intramedullary (IM) rod for bone fixation of the related art.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

Hereinafter, an intramedullary (IM) rod for bone fixation will be described according to an embodiment with reference to the accompanying drawings.

Figure 3:
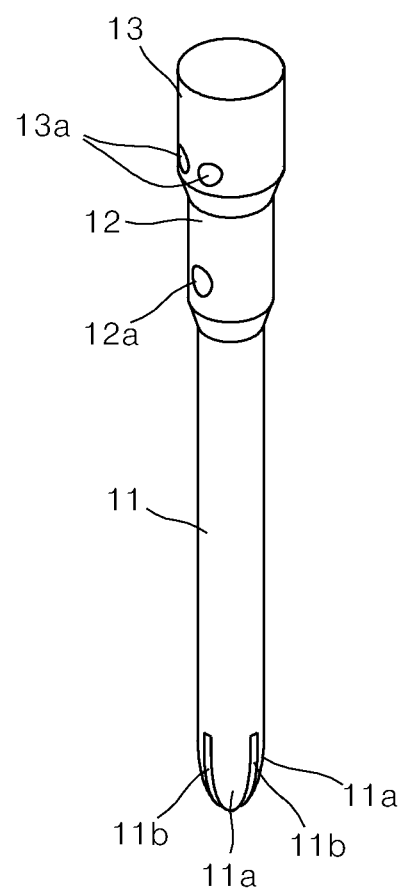
FIG. 3 is a perspective view illustrating an IM rod for bone fixation according to an embodiment.
Figure 4:
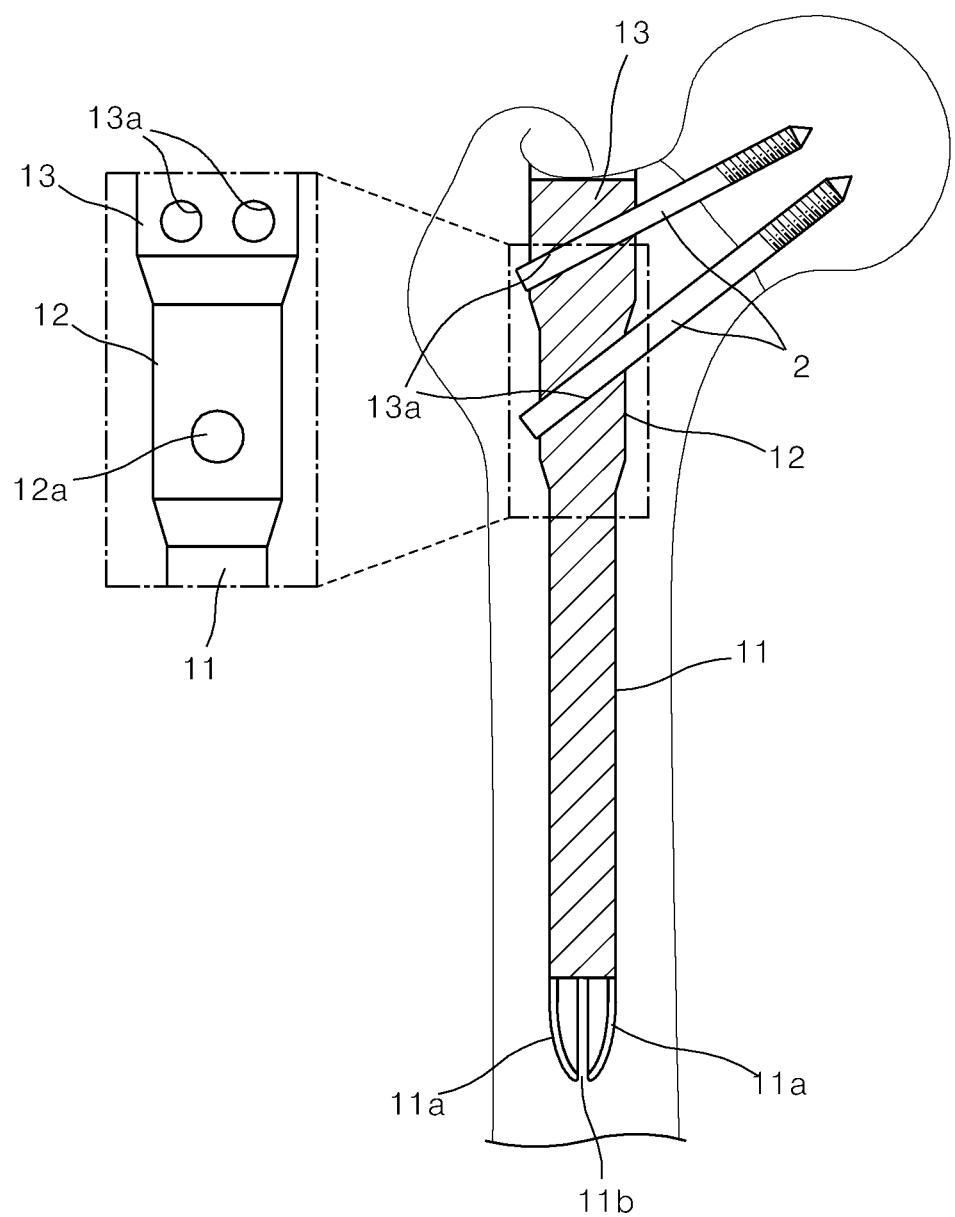
FIG. 4 is a cross-sectional view illustrating a use state according to the embodiment.
Figure 5:
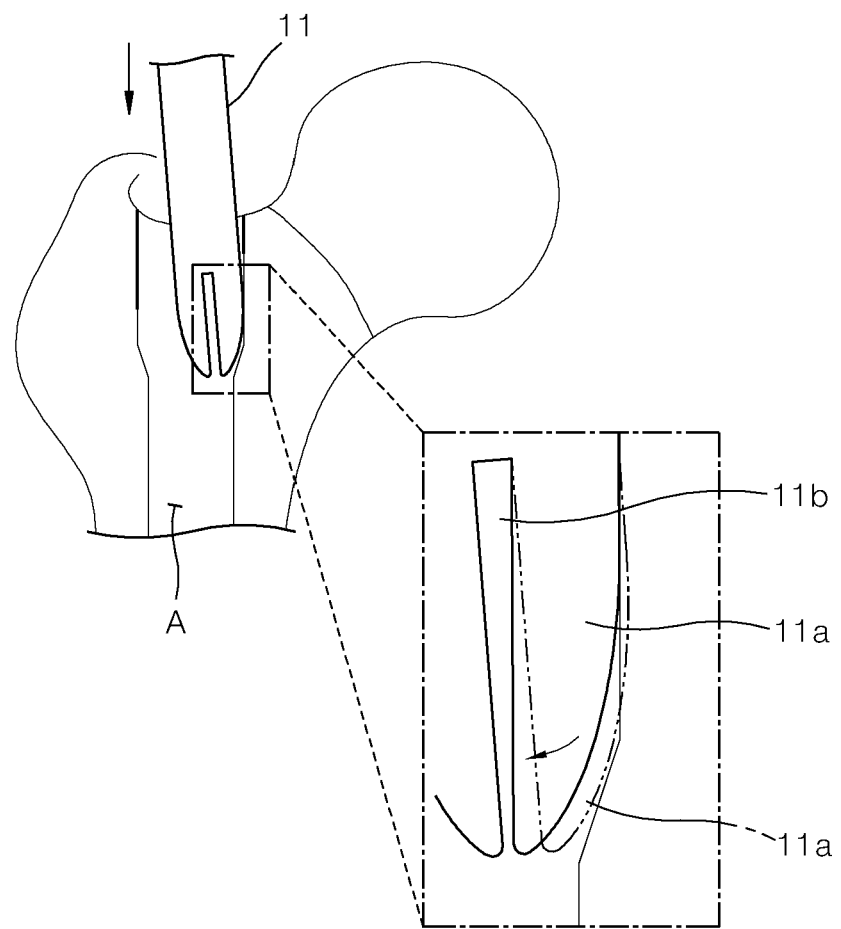
FIG. 5 is a view illustrating functions of deformable ribs according to the embodiment.

FIG. 3 is a perspective view illustrating an IM rod for bone fixation according to an embodiment, FIG. 4 is a cross-sectional view illustrating a use state according to the embodiment, and FIG. 5 is a view illustrating functions of deformable ribs according to the embodiment.

As clearly shown in FIGS. 3 and 4, the IM rod for bone fixation according to the embodiment is configured to be placed in the intramedullary cavity A (center portion, refer to FIG. 5) of a part of a fractured bone which is to be fixed to another part of the fractured bone, and for this end, the IM rod lengthily extends in the direction of the part of the fractured bone and includes a plurality of guide holes which guide fasteners 2 for fixing the parts of the fractured bone. The guide holes include a main hole 12a and a pair of sub-holes 13a to enable three-point support for improving fastening strength.

That is, as shown in an enlarged portion in FIG. 4, the guide holes include the main hole 12a and the pair of sub-holes 13a which are provided at positions forming the vertices of a triangle together with the main hole 12a, such that when parts of a fractured bone are fastened to each other using the fasteners 2, high fastening strength may be guaranteed.

In particular, since the IM rod for bone fixation and the fasteners 2 of the embodiment are configured to be implanted into the intramedullary cavity A, the IM rod and the fasteners 2 are generally designed to have a circular cross-sectional shape for reducing damage to the tissue of the body and smoothening the implanting process.

The IM rod and the fasteners 2 having a circular cross-sectional shape may be easily rotated because of their structures, and thus after parts of a fractured bone are fastened to each other using the IM rod and the fasteners 2, the fastened state of the fractured bone in tissue may loosen with time. To overcome this, an IM rod enabling the use of a plurality of fasteners along the same axial line has been developed. However, even the IM rod tilts with respect the axial line, and thus a fastened state may not be securely maintained.

According to the embodiment, however, the IM rod for bone fixation includes the guide holes through which the fasteners 2 are inserted for fixing parts of a fractured bone, and the guide holes include the main hole 12a at a center position and the pair of sub-holes 13a provided at certain intervals at eccentric positions with respect to the main hole 12a. Therefore, fastening support points by the fasteners 2 may form the vertices of a triangle owing to the main hole 12a and the pair of sub-holes 13a, and bone fastening strength of the fasteners 2 of the embodiment may be maintained for a long time.

According to the current embodiment, the IM rod includes an intermediate diameter portion 12, a large diameter portion 13, and a small diameter portion for optimal design of the main hole 12a and the pair of sub-holes 13a.

That is, the intermediate diameter portion 12 is a portion in which the main hole 12a of the guide holes is formed, and the large diameter portion 13 is a portion in which the pair of sub-holes 13a of the guide holes are formed and having a diameter greater than the diameter of the intermediate diameter portion 12.

The small diameter portion 11 is a portion in which the main hole 12a and the pair of sub-holes 13a are not formed and which lengthily extends from the intermediate diameter portion 12 in an axial directional and has a diameter less than the diameter of the intermediate diameter portion 12 for being smoothly inserted into the intramedullary cavity A according to the embodiment.

According to the current embodiment having the configuration, the small diameter portion 11, which is a portion to be placed in the intramedullary cavity A, is designed to have the smallest diameter to reduce damage to tissue in the intramedullary cavity A and enable smooth implantation into the intramedullary cavity A, and the intermediate diameter portion 12 in which the main hole 12a is formed and the large diameter portion 13 in which the pair of sub-holes 13a are formed are designed to have diameters different from each other to enable three-point support without interfering with the implantation into the intramedullary cavity A.

As clearly shown in FIG. 5, the small diameter portion 11 includes deformable ribs 11a between which a plurality of deformable slits 11b are formed to allow bending deformation between adjacent elements, such that when the IM rod of the embodiment is implanted into a bone, the inner wall of the center portion of the bone may not be damaged by friction.

That is, the small diameter portion 11 is placed in the intramedullary cavity A through a small hole, and since the small diameter portion 11 has a relatively long shape, the inner wall of the bone may be damaged by collision with the small diameter portion 11 as shown in an enlarged portion of FIG. 5.

However, according to the current embodiment, since the deformable ribs 11a of the small diameter portion 11 are designed to be bendable, even when the deformable ribs 11a collide with the inner wall of the bone, the deformable ribs 11a may not apply a large impact force to the bone and reduce the impact of collision while being deformed.

Figure 6:
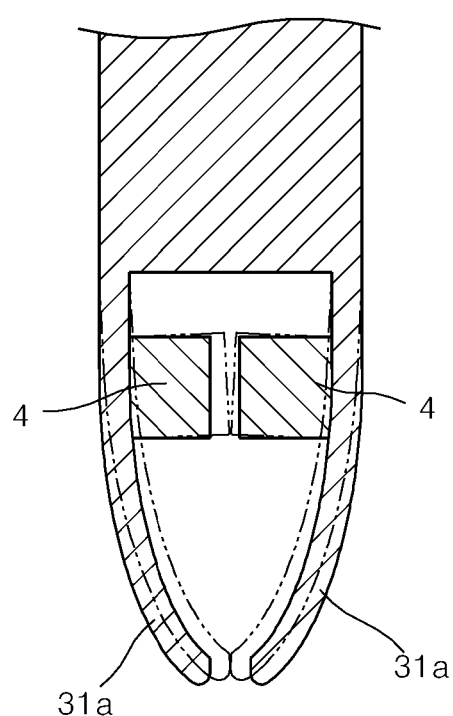
FIG. 6 is a cross-sectional view illustrating structures of deformable ribs according to another embodiment.

In addition, FIG. 6 is a cross-sectional view illustrating structures of deformable ribs 31a according to another embodiment.

In the embodiment shown in FIG. 6, a plurality of buffer members 4 are provided on mutually-facing inner surfaces of the deformable ribs 31a at mutually contactable and separable positions.

Each of the buffer members 4 includes a buffering material such as silicone harmless to the human body such that the buffer members 4 may perform a buffering function when being brought into contact with each other and may return to their original shapes when being separated from each other.

According to the current embodiment, even when the deformable ribs 31a include a flexible material to guarantee a greater amount of bending deformation, the deformable ribs 31a may smoothly return to their original shape after deformation owing to the buffer members 4, and thus damage to the intramedullary cavity may be reduced during implantation.

Figure 7:
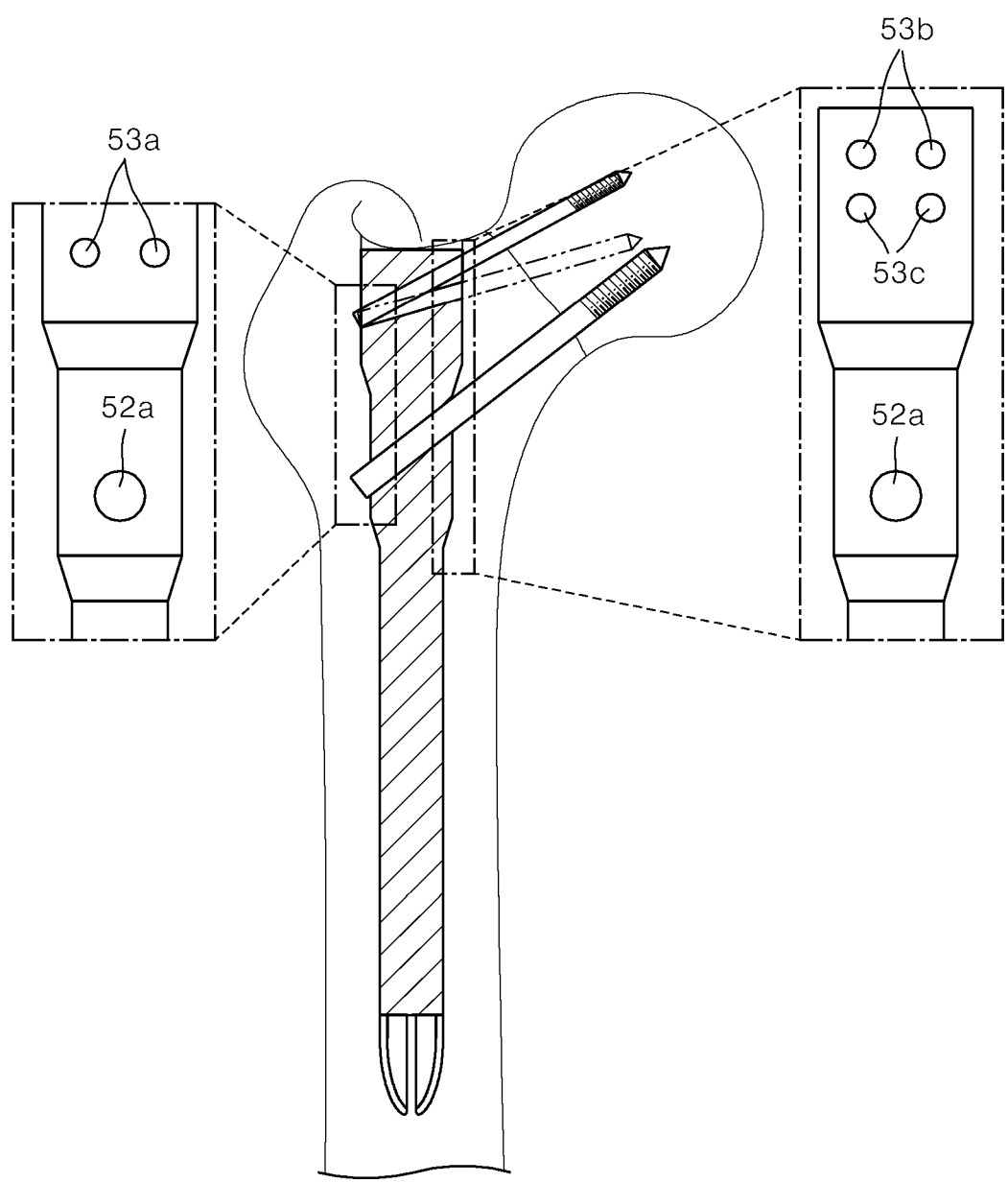
FIG. 7 is a cross-sectional view illustrating a structure and a use state according to another embodiment.

FIG. 7 is a cross-sectional view illustrating a structure and a use state according to another embodiment.

As shown in FIG. 7, in the current embodiment, guide holes include a main hole 52a, a pair of entrance-side sub-holes 53a, and two pairs of exit-side sub-holes 53b and 53c.

According to the current embodiment having this configuration, a clinician may select a pair corresponding to the entrance-side sub-holes 53a from the pairs of exit-side sub-holes 53b and 53c by considering the angle for fixing parts of a fractured bone (the pair of exit-side sub-holes 53b may be selected when the angle of fasteners is required to be as shown by a solid line, and the pair of exit-side sub-holes 53c may be selected when the angle of fasteners is required to be as shown by a two-dot chain line), and thus the fastening angle of the fasteners may be smoothly adjusted to a required value. Therefore, clinicians' convenience and precision in medical procedures may be improved.

In addition, although the number of entrance-side sub-holes 53a is two and the number of exit-side sub-holes 53b and 53c is four in the current embodiment, the present disclosure is not limited thereto. For example, the number of entrance-side sub-holes 53a may be four, and the number of exit-side sub-holes 53b and 53c may be two.

In addition, when the current embodiment is applied to a bilaterally symmetric structure, a clinician may select whether to use the entrance-side sub-holes 53a as an entrance or an exit, and thus medical procedures may be performed more precisely and conveniently.

As described above, the IM rod for bone fixation of the present disclosure includes guide holes through which fasteners are inserted to fix parts of a fractured bone, and the guide holes include a main hole at a center position and a pair of sub-holes at certain intervals at eccentric positions with respect to the main hole, such that fastening support positions of the fasteners may form the vertices of a triangle owing to the main hole and the pair of sub-holes. Therefore, the fastening strength of the IM rod and the fasteners may be maintained for a long time.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. An intramedullary (IM) rod for bone fixation, the IM rod being configured to be placed in an intramedullary cavity of a center portion of a part of a fractured bone which is required to be fixed to another part of the fractured bone, the IM rod lengthily extending in a direction of the part of the fractured bone, wherein the IM rod comprises:
   a plurality of guide holes configured to guide fasteners which are inserted through the part of the fractured bone and fastened to the other part of the fractured bone, wherein plurality of guide holes comprises a main hole and a pair of sub-holes provided at positions forming vertices of a triangle together with the main hole;
   an intermediate diameter portion in which the main hole of the plurality of guide holes is formed;
   a large diameter portion in which the pair of sub-holes of the plurality of guide holes are formed and having a diameter greater than a diameter of the intermediate diameter portion;
   a small diameter portion lengthily extending in an axial direction from the intermediate diameter portion and having a diameter less than the diameter of the intermediate diameter portion, wherein the small diameter portion comprises deformable ribs between which a plurality of deformable slits are formed to allow bending deformation between adjacent elements such that damage caused by friction with an inner wall of the center portion of the part of the fractured bone is suppressed; and
   a plurality of buffer members provided on mutually-facing inner surfaces of the deformable ribs at mutually contactable and separable positions, the plurality of buffer members comprising a buffering material such that the plurality of buffer members perform a buffering function when being brought into contact with each other and return to original shapes thereof when being separated from each other.

2. The IM rod of claim 1, wherein the plurality of guide holes further comprises:
   two pairs of exit-side sub-holes forming different lines together with the pair of sub-holes to adjust a fastening angle of the fasteners inserted through the pair of sub-holes.

* * * * *